US010793832B2

(12) United States Patent
Matsumoto et al.

(10) Patent No.: US 10,793,832 B2
(45) Date of Patent: *Oct. 6, 2020

(54) PANCREATIC ENDOCRINE CELLS, METHOD FOR PRODUCING SAME, AND TRANSDIFFERENTIATION AGENT

(71) Applicant: Juntendo Educational Foundation, Tokyo (JP)

(72) Inventors: Masahito Matsumoto, Saitama (JP); Yasushi Okazaki, Saitama (JP); Izumi Sugahara, Saitama (JP)

(73) Assignee: Juntendo Educational Foundation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/243,865

(22) Filed: Jan. 9, 2019

(65) Prior Publication Data

US 2019/0127704 A1 May 2, 2019

Related U.S. Application Data

(63) Continuation of application No. 15/323,576, filed as application No. PCT/JP2015/069296 on Jul. 3, 2015, now Pat. No. 10,214,728.

(30) Foreign Application Priority Data

Jul. 3, 2014 (JP) ................. 2014-137719

(51) Int. Cl.
 *C12N 5/071* (2010.01)

(52) U.S. Cl.
 CPC ........ *C12N 5/0676* (2013.01); *C12N 2501/60* (2013.01); *C12N 2506/02* (2013.01); *C12N 2506/1307* (2013.01); *C12N 2506/14* (2013.01); *C12N 2506/25* (2013.01); *C12N 2506/30* (2013.01); *C12N 2510/00* (2013.01); *C12N 2799/06* (2013.01)

(58) Field of Classification Search
 CPC ............................................. C12N 2506/1307
 See application file for complete search history.

(56) References Cited

U.S. PATENT DOCUMENTS

| 8,927,277 B2 | 1/2015 | Yamanaka et al. |
| 2003/0077259 A1 | 4/2003 | Levine et al. |
| 2009/0280096 A1 | 11/2009 | Kubo et al. |
| 2011/0112015 A1 | 5/2011 | Julier et al. |

FOREIGN PATENT DOCUMENTS

| JP | 2003-245067 | 9/2003 |
| JP | 2005-506072 | 3/2005 |
| JP | 2009533047 | 9/2009 |
| JP | 2013519371 | 5/2013 |
| WO | 03078636 | 9/2003 |

OTHER PUBLICATIONS

International Search Report issued in International Application No. PCT/JP2015/069296 dated Sep. 8, 2015 (5 pages; English translation).
Written Opinion issued in International Application No. PCT/JP2015/069296 dated Sep. 8, 2015 (8 pages).
Kang H.S. et al.: "Transcription factor Glis3, a Novel Critical Player in the Regulation of Pancreatic β-cell development and insulin gene expression"; Molecular and Cellular Biology, Dec. 2009, vol. 29, No. 24, pp. 6366-6379.
Kim Y.S. et al.: "Glis3 regulates neurogin 3 expression in pancreatic β-cells and interacts with its activator"; Mol. Cells, 2012, vol. 34, No. 2, pp. 193-200.
Yang Y. et al.: "The Krueppel-like zinc finger protein GLIS3 transactivates neurogin 3 for proper fetal pancreatic islet differentiation in mice"; Diabetologia; 2011, vol. 54, No. 10, pp. 2595-2605.
Supplementary European Search Report issued in corresponding European Application No. 15815940.0 dated Dec. 13, 2017. (10 pages).
Akinici et al.: "Reprogramming of pancreatic exocrine cells towards a beta (β) cell character using Pdx1, Ngn3, and MafA", Biochemical Journal, 2012, vol. 442, pp. 539-550 (16 pages).
Maekawa et al.: "Direct reprogramming of somatic cells is promoted by maternal transcription factor Glis1", Nature, 2011, vol. 474, pp. 225-229.
Mfopou et al.: "recent Advances and Prospects in the Differentiation of Pancreatic Cells from Human Embryonic Stem Cells", Diabetes, American Diabetes Association, 2010, vol. 59, pp. 2094-2101.
Scoville et al.: "GLIS1-3: emerging roles in reprogramming, stem and progenitor cell differentiation and maintenance", Stem Cell Investigation, 2017, vol. 4, 11 pages.
Office Action issued in Japanese Patent Application No. 2016-531476, dated Nov. 26, 2019, 4 pages with translation.
Office Action issued in corresponding Japanese Patent Application No. 2016-531476, dated Jul. 14, 2020, 4 pages with translation.

*Primary Examiner* — Bin Shen
(74) *Attorney, Agent, or Firm* — Hamre, Schumann, Mueller & Larson, P. C.

(57) ABSTRACT

A method for producing pancreatic endocrine cells, the method including
 introducing one or more genes of a GLIS family or one or more gene products thereof and a Neurogenin3 gene or one or more gene products thereof into somatic cells.

8 Claims, 11 Drawing Sheets

Specification includes a Sequence Listing.

SEQUENCE LISTING

```
<160> NUMBER OF SEQ IDS NOS: 8

<210> SEQ ID NO 1
<211> LENGTH: 21
<212> TYPE: DNA
<213> ORGANISM: Artificial Sequence
<220> FEATURE:
<223> OTHER INFORMATION: primer

<400> SEQUENCE: 1
tggagaaacc tgccaagtat g                                              21

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
ggagacaacc tggtcctcag                                                20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
tttgtcaagc agcacctttg                                                20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
ggtctgaagg tcacctgctc                                                20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
atgttcgtca tgggtgtgaa                                                20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
tgtggtcatg agtccttcca                                                20

<210> SEQ ID NO 7
<211> LENGTH: 20
<212> TYPE: DNA
<213> ORGANISM: Artificial Sequence
```

```
<220> FEATURE:
<223> OTHER INFORMATION: primer

<400> SEQUENCE: 7
gccatcaagc agatcactgt                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
caggtgttgg ttcacaaagg                                               20
```

PANCREATIC ENDOCRINE CELLS, METHOD FOR PRODUCING SAME, AND TRANSDIFFERENTIATION AGENT

This application is a continuation of Ser. No. 15/323,576, filed Jan. 3, 2017, now U.S. Pat. No. 10,214,728, which is a national stage of PCT/JP2015/069296, filed Jul. 3, 2015.

TECHNICAL FIELD

The present invention relates to a method for producing pancreatic endocrine cells from somatic cells, pancreatic endocrine cells produced by the method, and a transdifferentiation agent that transdifferentiates somatic cells to pancreatic endocrine cells.

BACKGROUND ART

Pancreatic endocrine cells have been expected to be used as, for example, a material for regenerative therapies for diabetes or a material used for screening of diabetes drugs. In terms of the regenerative therapies, for example, it has been expected that β cells, which are one of the pancreatic endocrine cells and produce insulin, are administered to type I diabetes patients who are insulin-deficient.

Therefore, keen demand has arisen for developing a method for preparing pancreatic endocrine cells in vitro in large quantities.

There has been proposed a method for producing β cells using embryonic stem cells (hereinafter may be referred to as "ES cells") or induced pluripotent stem cells (hereinafter may be referred to as "iPS cells"). However, the method has the following problems. Firstly, the method is complicated because culturing environments are needed to be properly adjusted by, for example, adding various inhibitors involved in development or differentiation to a cell culture medium. Secondly, the method may be unreproducible. Thirdly, the method is problematic in terms of efficiency because other cells than the β cells are also produced. Finally, the method takes at least 21 days to 30 days to produce the β cells, that is, the β cells are not capable of being produced in a short period of time.

Therefore, at present, keen demand has arisen for promptly providing a method for producing pancreatic endocrine cells, the method being simple, easily reproduced, excellent in production efficiency, and capable of producing the pancreatic endocrine cells in a short period of time.

Note that, GLIS1 (GLIS family zinc finger 1), which is a member of the GLIS family, has been known to improve an establishment improving efficiency of iPS cells (see, e.g., PTL 1). GLIS3 (GLIS family zinc finger 3) has been known to be capable of being used for inducing differentiation of human pluripotent or multipotent cells into functional pancreatic β cells that produce insulin (see, e.g., PTL 2). Ngn3 (Neurogenin3) has been known to be transiently expressed in pancreatic endocrine cells during pancreas development.

However, it has not been that the GLIS family or the Ngn3 transform somatic cells into pancreatic endocrine cells directly without undergoing the stem cell stage.

CITATION LIST

Patent Literature

PTL 1: Japanese Patent Application Laid-Open (JP-A) No. 2013-519371.
PTL 2: JP-A No. 2009-533047

SUMMARY OF INVENTION

Technical Problem

The present invention aims to solve the above existing problems and achieve the following object. That is, the present invention has an object to provide a method for producing pancreatic endocrine cells, the method being simple, easily reproduced, excellent in production efficiency, and capable of producing the pancreatic endocrine cells in a short period of time; pancreatic endocrine cells produced by the method; and a transdifferentiation agent that transdifferentiates somatic cells to pancreatic endocrine cells.

Solution to Problem

Means for solving the above problems are as follows.
<1> A method for producing pancreatic endocrine cells, the method including
 introducing one or more genes of a GLIS family or one or more gene products thereof and a Neurogenin3 gene or one or more gene products thereof into somatic cells.
<2> Pancreatic endocrine cells produced by the method for producing pancreatic endocrine cells according to <1>.
<3> A transdifferentiation agent including:
 one or more genes of a GLIS family or one or more gene products thereof; and
 a Neurogenin3 gene or one or more gene products thereof,
 wherein the transdifferentiation agent is configured to transdifferentiate somatic cells into pancreatic endocrine cells.

Advantageous Effects of Invention

According to the present invention, it is possible to solve the above existing problems and achieve the above object. That is, the present invention can provide a method for producing pancreatic endocrine cells, the method being simple, easily reproduced, excellent in production efficiency, and capable of producing the pancreatic endocrine cells in a short period of time; pancreatic endocrine cells produced by the method; and a transdifferentiation agent that transdifferentiates somatic cells to pancreatic endocrine cells.

Figure 1:
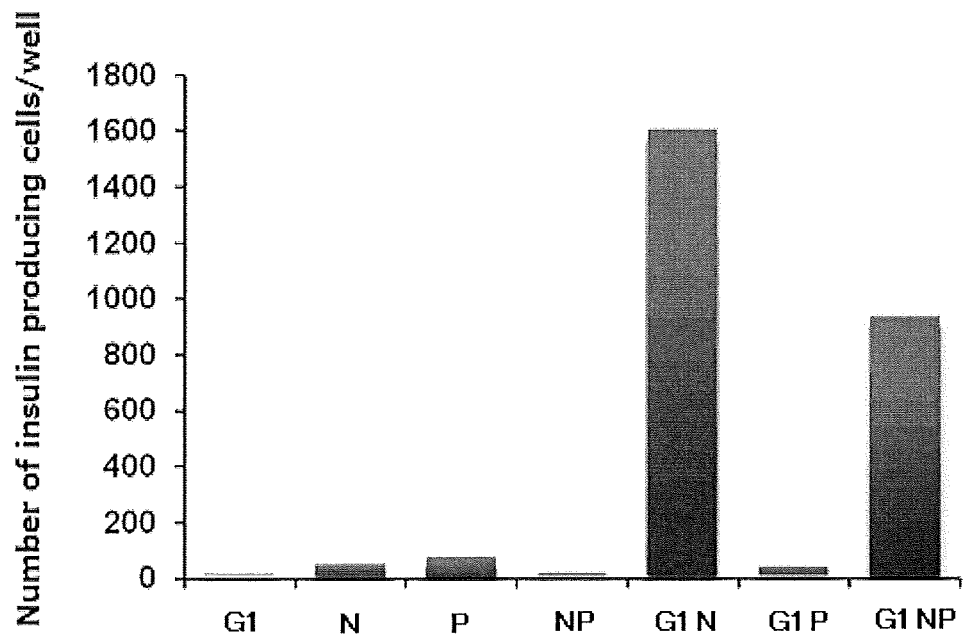
FIG. 1 is a graph illustrating the measurement results of the number of DsRed2-positive insulin producing cells 12 days after viral infection in Test Examples 1.

DESCRIPTION OF EMBODIMENTS (Pancreatic Endocrine Cells and Production Method Thereof)

Pancreatic endocrine cells of the present invention are capable of being produced by a method for producing pancreatic endocrine cells of the present invention.

The pancreatic endocrine cells of the present invention will now be described in conjunction with the method for producing pancreatic endocrine cells of the present invention.

<Production Method of Pancreatic Endocrine Cells>

The method for producing pancreatic endocrine cells of the present invention includes at least an introduction step; and, if necessary, further includes other steps.

<<Introduction Step>>

The introduction step is a step of introducing one or more genes of a GLIS family or one or more gene products thereof and an Ngn3 gene or one or more gene products thereof into somatic cells.

The gene products refer to mRNAs transcribed from genes or proteins translated from the mRNAs.

—Genes or One or More Gene Products Thereof—

The genes or one or more gene products thereof to be introduced into the somatic cells in the introduction step include at least one or more genes of a GLIS family or one or more gene products thereof and an Ngn3 gene or one or more gene products thereof; and, if necessary, further include other genes or one or more gene products thereof.

——One or More Genes of GLIS Family——

A source of the one or more genes of the GLIS family is not particularly limited and may be appropriately selected depending on the intended purpose. Examples thereof include human and mouse.

The one or more genes of the GLIS family are not particularly limited and may be appropriately selected depending on the intended purpose. Examples thereof include GLIS1, GLIS2, and GLIS3. These may be used alone or in combination. Among the one or more genes of the GLIS family, GLIS1 and GLIS3 are preferable, and GLIS1 is more preferable from the viewpoint of excellent production efficiency of the pancreatic endocrine cells.

Sequence information of the one or more genes of the GLIS family is available from known databases. For example, the sequence information is available from NCBI under Accession numbers of NM_147193 (human GLIS1), NM_147221 (mouse GLIS1), NM_032575 (human GLIS2), NM_031184 (mouse GLIS2), NM_152629 (human GLIS3), NM_175459, and NM_172636 (mouse GLIS3).

——Ngn3 Gene——

A source of the Ngn3 gene is not particularly limited and may be appropriately selected depending on the intended purpose. Examples thereof include human and mouse.

Sequence information of the Ngn3 gene is available from known databases.

For example, the sequence information is available from NCBI under Accession numbers of NM_009719 (mouse) and NM_020999 (human).

——Other Genes or One or More Gene Products Thereof——

The other genes or one or more gene products thereof are not particularly limited and may be appropriately selected depending on the intended purpose, so long as they do not impair effects of the present invention. A Pdx1 gene or one or more gene products thereof are preferable.

——Pdx1 Gene——

A source of the Pdx1 gene is not particularly limited and may be appropriately selected depending on the intended purpose. Examples thereof include human and mouse.

Sequence information of the Pdx1 gene is available from known databases. For example, the sequence information is available from NCBI under Accession numbers of NM_000209 (human) and NM_008814 (mouse).

Each of sequences of the one or more genes of the GLIS family or one or more gene products thereof, the Ngn3 gene or one or more gene products thereof, and the other genes or one or more gene products thereof may consist of a region to be translated into a protein in the sequence of each of the genes, or may include other regions than the region to be translated into a protein. Each of the genes or one or more gene products thereof may have a mutation.

Examples of the mutation include mutations that do not change an amino acid sequence of a protein from each of the genes and mutations in which one or several (2 to 5) amino acids are deleted, substituted, inserted, or added in an amino acid sequence of a protein from each of the genes.

In the case where each of the genes or one or more gene products thereof has a mutation, a sequence homology to each of corresponding wild-type genes or one or more gene products thereof is not particularly limited and may be appropriately selected depending on the intended purpose, but is preferably 70% or more, more preferably 80% or more, particularly preferably 90% or more in a base sequence of the region to be translated into a protein.

The genes or one or more gene products thereof to be introduced into the somatic cells in the introduction step are not particularly limited and may be appropriately selected depending on the intended purpose, so long as they include at least the one or more genes of the GLIS family or one or more gene products thereof and the Ngn3 gene or one or more gene products thereof. However, the genes or one or more gene products thereof preferably consist of (1) the one or more genes of the GLIS family or one or more gene products thereof and the Ngn3 gene or one or more gene products thereof or (2) the one or more genes of the GLIS family or one or more gene products thereof, the Ngn3 gene or one or more gene products thereof, and the Pdx1 gene or one or more gene products thereof, from the viewpoints of higher simplicity, easiness of reproduction, excellent production efficiency, and production of the pancreatic endocrine cells in a short period of time.

—Somatic Cells—

The somatic cells are not particularly limited and may be appropriately selected depending on the intended purpose. The somatic cells may be undifferentiated precursor cells or terminally differentiated mature cells.

The somatic cells may be derived from ES cells or iPS cells.

Specific examples of the somatic cells include adipose tissue-derived interstitial (stem) cells, neural stem cells, hematopoietic stem cells, mesenchymal stem cells, fibroblasts, hepatic cells, epithelial cells, renal cells, macrophages, lymphocytes, and muscle cells. Among them, fibroblasts, mesenchymal stem cells, hepatic cells, epithelial cells, and renal cells are preferable, and fibroblasts and mesenchymal stem cells are more preferable.

A species of an individual from which the somatic cells are harvested is not particularly limited and may be appropriately selected depending on the intended purpose. Examples thereof include human and mouse.

An individual from which the somatic cells are harvested is not particularly limited and may be appropriately selected depending on the intended purpose. In the case where the resultant pancreatic endocrine cells are used for regenerative therapies, the individual is preferably the individual oneself or other individuals having the same or substantially the same MHC type as that of the individual, in terms of a rejection reaction. The phrase "substantially the same MHC type" means, as used herein, that the MHC type is compatible to the extent that, when pancreatic endocrine cells derived from the somatic cells are transplanted into an individual, transplanted cells are capable of being engrafted with the use of, for example, an immunosuppressive agent.

A time when the somatic cells are harvested from the individual is not particularly limited and may be appropriately selected depending on the intended purpose.

A condition under which the somatic cells are cultured is not particularly limited and may be appropriately selected depending on the intended purpose. Examples thereof include a culturing temperature of about 37° C. and a $CO_2$ concentration of from about 2% to about 5%.

A medium in which the somatic cells are cultured is not particularly limited and may be appropriately selected depending on the intended purpose. Examples thereof include minimum essential media (hereinafter may be referred to as "MEM"), Dulbecco's modified Eagle media (hereinafter may be referred to as "DMEM"), RPMI1640 media, 199 media, and F12 media, all of which contain from 5% by mass to 20% by mass of serum.

—Introduction Method—

A method for introducing each of the genes or one or more gene products thereof into the somatic cells is not particularly limited and may be appropriately selected depending on the intended purpose. For example, vectors, synthetic mRNA (messenger RNA), or recombinant proteins may be used.

——Vector——

The vector is not particularly limited and may be appropriately selected depending on the intended purpose. Examples thereof include viral vectors and non-viral vectors.

Specific examples of the viral vectors include retroviral vectors and lentiviral vectors.

Specific examples of the non-viral vectors include plasmid vectors and episomal vectors.

A method for introducing the vector into the somatic cells is not particularly limited and may be appropriately selected from known methods in the art.

In the case where the retroviral vectors are used, the methods described in, for example, WO 2007/69666; Cell, 126, 663-676 (2006); or Cell, 131, 861-872 (2007) may be used. In the case where the lentiviral vectors are used, the methods described in, for example, Science, 318, 1917-1920 (2007).

In the case where the plasmid vectors are used, the methods described in, for example, Science, 322, 949-953 (2008). In the case where the episomal vectors are used, the methods described in, for example, Science, 324: 797-801 (2009) or Biochemical and Biophysical Research Communications, 426: 141-147 (2012).

In the case where the viral vectors are used, viral particles obtained using packaging cells may be used.

The packaging cells are cells into which viral structural protein-coding genes have been introduced. When a recombinant viral vector into which a target gene has been incorporated is introduced into the cells, recombinant viral particles into which the target gene has been incorporated are produced.

The packaging cells are not particularly limited and may be appropriately selected depending on the intended purpose. Examples thereof include packaging cells based on human kidney-derived HEK293 cells or mouse fibroblast-derived NIH3T3 cells; packaging cells Platinum-E (hereinafter may be referred to as "Plat-E cells") which are capable of producing high titer viruses for a long period of time and in which viral structural proteins gag-pol and env are expressed under the control of MoMuLV (Moloney Murine Leukemia Virus) LTR (long terminal repeats); PLAT-A cells that are designed to express Amphotropic virus-derived envelope glycoproteins; and PLAT-GP cells that are designed to express vesicular stomatitis virus-derived envelope glycoproteins.

A method for introducing the viral vector into the packaging cells is not particularly limited and may be appropriately selected depending on the intended purpose. Examples thereof include lipofection methods, electroporation methods, and calcium phosphate methods.

A method for infecting the somatic cells with the resultant viral particles is not particularly limited and may be appropriately selected depending on the intended purpose. Examples thereof include polybrene methods.

The vector may include a marker gene for verifying whether each of the genes has been successfully introduced.

The marker gene refers to a gene that allows for cell sorting or cell selection by introducing the marker gene into a cell. Specific examples of the marker gene include drug resistant genes, fluorescent protein genes, luminescent enzyme genes, and coloring enzyme genes. These may be used alone or in combination.

Specific examples of the drug resistant genes include neomycin resistant genes, tetracycline resistant genes, kanamycin resistant genes, zeocin resistant genes, and hygromycin resistant genes.

Specific examples of the fluorescent protein genes include green fluorescent protein (GFP) genes, yellow fluorescent protein (YFP) genes, and red fluorescent protein (RFP) genes.

Specific examples of the luminescent enzyme gene include luciferase genes.

Specific examples of the coloring enzyme genes include β galactosidase genes, β glucuronidase genes, and alkaline phosphatase genes.

In a method for introducing each of the genes into the somatic cells using the vector, one gene may be incorporated into one vector, or two or more genes may be incorporated into one vector. By incorporating two or more genes into one vector, the two or more genes may be expressed at the same time (hereinafter may be referred to as "co-expression").

A method for incorporating two or more genes into one vector is not particularly limited and may be appropriately selected depending on the intended purpose. However, the two or more genes are preferably incorporated via a linkage sequence.

The linkage sequence is not particularly limited and may be appropriately selected depending on the intended purpose. Examples thereof include gene sequences coding for a foot and mouth disease virus (Picornaviridae Aphthovirus)-derived 2A peptide and IRESs (internal ribosome entry sites).

A method for introducing the mRNA into the somatic cells is not particularly limited and may be appropriately selected from known methods in the art.

A method for introducing the recombinant protein into the somatic cells is not particularly limited and may be appropriately selected from known methods in the art.

The number of times of introduction of each of the genes or one or more gene products thereof into the somatic cells is not particularly limited and may be appropriately selected depending on the intended purpose. For example, each of the genes or one or more gene products thereof may be introduced once or two or more times.

A time when each of the genes or one or more gene products thereof are introduced into the somatic cells is not particularly limited and may be appropriately selected depending on the intended purpose. The genes or one or more gene products thereof may be introduced at the same time or at different times.

An amount of each of the genes or one or more gene products thereof to be introduced into the somatic cells is not particularly limited and may be appropriately selected depending on the intended purpose. The genes or one or more gene products thereof may be introduced in an equal amount or different amounts.

The genes or one or more gene products thereof to be used may be the genes only, the gene products only, or both of the genes and the gene products.

The genes or one or more gene products thereof may be combined with a different gene or one or more gene products thereof. The combination is not particularly limited and may be appropriately selected depending on the intended purpose. The same combination or different combinations may be used for each of the genes or one or more gene products thereof.

In the introduction step of the genes or one or more gene products thereof, other materials than the genes or one or more gene products thereof may be introduced, so long as they do not impair effects of the present invention.

<<Other Steps>>

The other steps are not particularly limited and may be appropriately selected depending on the intended purpose, so long as they do not impair effects of the present invention. Examples thereof include a genes or genes products thereof-introduced cells culturing step in which somatic cells, into which each of the genes or one or more gene products thereof has been introduced, are cultured.

—Genes or Genes Products Thereof-Introduced Cells Culturing Step—

The genes or genes products thereof-introduced cells culturing step is a step of culturing somatic cells into which each of the genes or one or more gene products thereof has been introduced.

A condition under which the genes or genes products thereof-introduced cells are cultured is not particularly limited and may be appropriately selected depending on the intended purpose. Examples thereof include a culturing temperature of about 37° C. and a $CO_2$ concentration of from about 2% to about 5%.

A medium used for culturing the genes or genes products thereof-introduced cells is not particularly limited and may be appropriately selected depending on the intended purpose. Examples thereof include MEM media, DMEM media, RPMI1640 media, 199 media, and F12 media, all of which contain from 5% by mass to 20% by mass of serum.

A period of time of the genes or genes products thereof-introduced cells culturing step is not particularly limited and may be appropriately selected depending on the intended purpose.

An exchange frequency of the medium is not particularly limited and may be appropriately selected depending on the intended purpose. Examples thereof include every 2 days to 3 days.

<Pancreatic Endocrine Cells>

A method for verifying whether pancreatic endocrine cells are successfully produced by the method for producing pancreatic endocrine cells is not particularly limited and may be appropriately selected depending on the intended purpose. Examples thereof include a method in which expression of proteins to be expressed in the pancreatic endocrine cells is verified and a method in which expression of genes to be expressed in the pancreatic endocrine cells is verified.

For example, whether α cells of the pancreatic endocrine cells are produced is capable of being verified by the presence or absence of glucagon expression, whether β cells of the pancreatic endocrine cells are produced is capable of being verified by the presence or absence of insulin expression, and whether δ cells of the pancreatic endocrine cells are produced is capable of being verified by the presence or absence of somatostatin expression.

The method in which expression of proteins is verified is not particularly limited and may be appropriately selected from known methods in the art. Examples thereof include immunostaining analyses.

The method in which expression of genes is verified is not particularly limited and may be appropriately selected from known methods in the art. Examples thereof include quantitative PCR analyses.

According to the method for producing pancreatic endocrine cells of the present invention, the pancreatic endocrine cells are capable of being produced from somatic cells through transdifferentiation. Therefore, the method is advantageous in that the pancreatic endocrine cells are capable of being produced without undergoing the iPS cell stage that have a risk of forming tumors.

Note that, the transdifferentiation refers to direct transformation from a cell type to another cell type without undergoing the stem cell stage.

The method for producing pancreatic endocrine cells of the present invention is simple and easily reproduced because a gene or one or more gene products thereof only have to be introduced into somatic cells, and at the same time the pancreatic endocrine cells are capable of being produced efficiently in a short period of time. Moreover, the method for producing pancreatic endocrine cells of the present invention is also advantageous in that the pancreatic endocrine cells are capable of being produced without using a special medium of which culturing environments are properly adjusted by, for example, adding inhibitors involved in development to the medium.

The pancreatic endocrine cells may be α cells, β cells, δ cells, or mixtures thereof. Among them, β cells are preferable in terms of regenerative therapies for diabetes patients.

The pancreatic endocrine cells of the present invention are suitably available as pancreatic endocrine cells used for screening of diabetes drugs.

(Transdifferentiation Agent)

A transdifferentiation agent of the present invention is a transdifferentiation agent for transdifferentiating somatic cells into pancreatic endocrine cells. The transdifferentiation agent includes at least one or more genes of a GLIS family or one or more gene products thereof and an Ngn3 gene or one or more gene products thereof; and, if necessary, further includes other components.

<Somatic Cells>

Somatic cells to be targeted by the transdifferentiation agent and preferable aspects thereof are the same as those described under the section entitled "Production method of pancreatic endocrine cells."

<Pancreatic Endocrine Cells>

Pancreatic endocrine cells obtained using the transdifferentiation agent and preferable aspects thereof are the same as those described under the section entitled "Production method of pancreatic endocrine cells."

<One or More Genes of GLIS Family or One or More Gene Products Thereof>

The one or more genes of the GLIS family or one or more gene products thereof and preferable aspects thereof are the same as those described under the section entitled "Production method of pancreatic endocrine cells." The one or more genes of the GLIS family or one or more gene products thereof may also have the same mutation as those described under the section entitled "Production method of pancreatic endocrine cells."

An aspect of the one or more genes of the GLIS family or one or more gene products thereof in the transdifferentiation agent is not particularly limited and may be appropriately selected depending on the intended purpose. For example, the one or more genes of the GLIS family or one or more gene products thereof may be incorporated into a vector, or may be a synthetic mRNA or a recombinant protein.

The vector may be the same as those described under the section entitled "Production method of pancreatic endocrine cells."

The synthetic mRNA and the recombinant protein may be produced by any of known methods in the art.

<Ngn3 Gene or One or More Gene Products Thereof>

The Ngn3 gene or one or more gene products thereof are the same as those described under the section entitled "Production method of pancreatic endocrine cells." The Ngn3 gene or one or more gene products thereof may also have the same mutation as those described under the section entitled "Production method of pancreatic endocrine cells."

An aspect of the Ngn3 gene or one or more gene products thereof in the transdifferentiation agent is not particularly limited and may be appropriately selected depending on the intended purpose. For example, the Ngn3 gene or one or more gene products thereof may be incorporated into a vector, or may be a synthetic mRNA or a recombinant protein.

The vector may be the same as those described under the section entitled "Production method of pancreatic endocrine cells."

The synthetic mRNA and the recombinant protein may be produced by any of known methods in the art.

<Other Components>

The other components are not particularly limited and may be appropriately selected depending on the intended purpose, so long as they do not impair effects of the present invention. However, the other components preferably include a Pdx1 gene or one or more gene products thereof.

The Pdx1 gene or one or more gene products thereof are the same as those described under the section entitled "Production method of pancreatic endocrine cells." The Pdx1 gene or one or more gene products thereof may also have the same mutation those described under the section entitled "Production method of pancreatic endocrine cells."

An aspect of the Pdx1 gene or one or more gene products thereof in the transdifferentiation agent is not particularly limited and may be appropriately selected depending on the intended purpose. For example, the Pdx1 gene or one or more gene products thereof may be incorporated into a vector, or may be a synthetic mRNA or a recombinant protein.

The vector may be the same as those described under the section entitled "Production method of pancreatic endocrine cells."

The synthetic mRNA and the recombinant protein may be produced by any of known methods in the art.

The genes or one or more gene products thereof in the transdifferentiation agent may be divided into separate containers or may be placed in a single container. Alternatively, any number of the genes or one or more gene products thereof may be placed in each container.

An amount of each of the genes or one or more gene products thereof in the transdifferentiation agent is not particularly limited. The genes or one or more gene products thereof may be included in an equal amount or different amounts.

The transdifferentiation agent may be suitably used as a component of a kit for producing pancreatic endocrine cells.

The kit for producing pancreatic endocrine cells includes at least the transdifferentiation agent; and, if necessary, further includes other components.

The other components in the kit for producing pancreatic endocrine cells are not particularly limited and may be appropriately selected depending on the intended purpose, so long as they do not impair effects of the present invention. Examples thereof include packaging cells and media.

The packaging cells and the media may be the same as those described under the section entitled "Production method of pancreatic endocrine cells."

EXAMPLES

The present invention will now be described with reference to Test Examples described below, but the present invention is not limited thereto in any way.

Test Example 1: Production of Pancreatic Endocrine Cells from Mouse Fibroblasts-1

<Preparation of Cells>

Dual-labeled-mouse embryonic fibroblasts (hereinafter may be referred to as "dMEF"), which were one kind of somatic cells, were prepared in the following manner.

—Production of Genetically Modified Mice in which Pancreatic Endocrine Precursor Cells are Fluorescently Labeled with GFP—

Genetically modified mice in which pancreatic endocrine precursor cells are fluorescently labeled with GFP (mice expressing EGFP under the control of an Ngn3 gene promoter (Ngn3-eGFP)) were produced in the following manner.

A construct, in which a fusion protein gene of GFP and a nuclear localization signal (hereinafter may be referred to as "nls") was ligated downstream of the Ngn3 gene promoter (5 kb) isolated from a BAC clone, was microinjected into about 400 fertilized eggs to thereby produce genetically modified mice in which pancreatic endocrine precursor cells are fluorescently labeled with GFP.

—Production of Genetically Modified Mice in which Pancreatic β Cells are Fluorescently Labeled with DsRed2—

Genetically modified mice in which pancreatic β cells are fluorescently labeled with DsRed2 (mice expressing DsRed2 under the control of a rat insulin promoter (Ins-DsR)) were produced in the following manner.

A construct, in which a DsRed2 gene was ligated downstream of the rat insulin promoter (800 bp), was microinjected into about 400 fertilized eggs to thereby produce genetically modified mice in which pancreatic β cells are fluorescently labeled with DsRed2.

—Production of Dual-Labeled-Mouse Embryonic Fibroblasts—

The genetically modified mice in which pancreatic endocrine precursor cells are fluorescently labeled with GFP were crossed with the genetically modified mice in which pancreatic β cells are fluorescently labeled with DsRed2, and then male and female offspring mice (heterozygous) were crossed with each other to generate dual-labeled genetically modified mice (Ngn3-eGFP/Ins-DsR) that were confirmed to be homozygous by genomic southern blotting. Two pairs (male and female) of the homozygous dual-labeled genetically modified mice were crossed. At embryonic day 14.5, 16 embryos were removed from the uterus, and their blood was washed off with 10 mL of phosphate-buffered saline (containing 10 mg/mL kanamycin) in a 10 cm Petri dish within a clean bench. Then, the embryos were minced with a pair of scissors in 10 mL of DMEM (available from Sigma, # D5796; containing penicillin, streptomycin, and 10% FBS) in a 10 cm cell culture dish (available from TPP, #93150). The resultant minced embryonic tissue was transferred into a 15 mL tube and centrifuged at 1.4 krpm at room temperature for 4 min. The supernatant was discarded. The remaining pellet was added with and suspended in 1 mL of a 0.25% trypsin-containing EDTA solution (available from Wako Pure Chemical Industries, Ltd., #201-16945, containing 0.25% DNase I), and then incubated in a water bath at 37° C. The water bath was stirred by hand every 10 min. The minced embryonic tissue corresponding to one animal was well-suspended in 5 mL of DMEM (containing 10% FBS) in a 15 mL tube, transferred into 5 mL of DMEM in a 10 cm cell culture dish, and then incubated within an incubator with 5% $CO_2$ at 37° C. On the following day, the 10 mL DMEM (containing 10% FBS) was replaced with fresh medium and subsequently changed every 2 days. About 4 to about 5 days after, dMEFs in the confluent 10 cm culture dish were washed with 6 mL of phosphate-buffered saline (hereinafter may be referred to as "PBS"). One milliliter of a 0.25% trypsin-containing EDTA solution was added thereto, and incubated to within an incubator with 5% $CO_2$ at 37° C. for 2 min. Then, the cells were confirmed to be peeled off. Ten milliliters of DMEM (containing 10% FBS) was added thereto and the cells were well-suspended. The dMEFs for one culture dish were seeded onto new five 10 cm culture dishes and further cultured. After 5 to 6 days of culturing, the dMEFs were confirmed to be grown confluent and washed with 6 mL of PBS. One milliliter of a 0.25% trypsin/EDTA solution was added thereto, and incubated within an incubator with 5% $CO_2$ at 37° C. for 2 min. Then, the cells were confirmed to be peeled off. Six milliliters of DMEM (containing 10% FBS) was added thereto and the cells were well-suspended. The resultant suspension liquid was transferred into a 50 mL tube and centrifuged at 1.4 krpm at room temperature for 4 min. Then, the supernatant was discarded. The remaining cell pellet was added with and suspended in 10 mL of CELLBANKER (available from Takara Bio Inc., # CB011). The resultant suspension liquid was dispensed into vial tubes (0.5 mL per tube) and stored in a deep freezer at −145° C.

<Production of Retrovirus>

Plat-E cells in which viral structural proteins gag-pol and env, which were capable of producing high titer viruses for a long period of time, were expressed under the control of MoMuLV LTR and a plasmid DNA (pMX vector or pMX-puro vector) were used to produce a retrovirus in the following manner (Onishi, M., et. al., Exp. Hematol. 24, 324-329, 1996).

—Preparation of Plasmid DNA—

[pMX-GFP Vector]

A pMX-GFP vector is a vector in which a gene coding for a full-length GFP protein is inserted into a multi-cloning site of a pMX vector and a pMXpuro vector (obtained from The Institute of Medical Science, The University of Tokyo). Note that, the sequence of the gene coding for a full-length GFP protein is deposited in NCBI under Accession number L29345.

[pMX-GLIS1 Vector]

A pMX-GLIS1 vector is a vector in which a gene coding for a full-length GLIS1 protein is inserted into a multi-cloning site of a pMX vector (available from Addgene). Note that, the sequence of the gene coding for a full-length GLIS1 protein is deposited in NCBI under Accession number NM_147221.

[pMX-Neurogenin3 Vector]

A pMX-Neurogenin3 vector is a vector in which a gene coding for a full-length Neurogenin3 protein is inserted into a multi-cloning site of a pMX vector (obtained from The Institute of Medical Science, The University of Tokyo). Note that, the sequence of the gene coding for a full-length Neurogenin3 protein is deposited in NCBI under Accession number NM_009719.

[pMX-Pdx1 Vector]

A pMX-Pdx1 vector is a vector in which a gene coding for a full-length Pdx1 protein is inserted into a multi-cloning site of a pMX vector (obtained from The Institute of Medical Science, The University of Tokyo). Note that, the sequence of the gene coding for a full-length Pdx1 protein is deposited in NCBI under Accession number NM 008814.

—Production of Retrovirus—

The Plat-E cells were seeded in a 6-well plate (available from TPP, 92406), which had been coated (for 1 hour at 37° C. and 5% $CO_2$) with Poly-L-Lysine (available from Sigma, P8920) diluted 10 fold with PBS, at $8 \times 10^5$ cells per well, and cultured overnight.

On the following day, 4 μg of the plasmid DNA was placed into a 1.5 mL tube containing 250 μL of OPTI-MEM (registered trademark) (available from Life Technologies Corporation, 11058021), mixed by tapping, and left to stand at room temperature for 5 min (hereinafter may be referred to as "plasmid/OPTI-MEM solution"). Meanwhile, 10 μL of LIPOFECTAMINE (registered trademark) 2000 (LP2000) (available from Life Technologies Corporation, 11668500) was placed into another 1.5 mL tube containing 250 μL of OPTI-MEM, mixed together, and left to stand at room temperature for 5 min (hereinafter may be referred to as "LP2000/OPTI-MEM solution"). The plasmid/OPTI-MEM solution and the LP2000/OPTI-MEM solution were well-mixed together and left to stand at room temperature for 20 min (hereinafter may be referred to as "plasmid/LP2000/OPTI-MEM mixed solution").

The plasmid/LP2000/OPTI-MEM mixed solution in which liposome-DNA complexes had been formed was added to one well in the 6-well plate, in which the Plat-E cells seeded the previous day had been cultured, to thereby transfect the cells. After mixing, the cells were cultured within an incubator with 5% $CO_2$ at 37° C. overnight. Twenty-four hours after, the medium was replaced, 1.5 mL of fresh DMEM (containing 10% FBS) was added thereto, and further cultured for 24 hours.

Forty-eight hours after the transfection, the culture supernatant containing viral particles was collected in a 2.5 mL syringe (available from Terumo Corporation, SS-02SZ) and filtered through a 0.45 filter (available from Whatman, PURADISC FP30 (CA-S 0.45 m), 10462100) to thereby remove the Plat-E cells. The culture supernatant containing viral particles were transferred into a 2.0 mL tube.

Thus, a pMX-GLIS1 vector-derived viral solution, a pMX-Neurogenin3 vector-derived viral solution, a pMX-Pdx1 vector-derived viral solution, and a pMX-GFP vector-derived viral solution were obtained.

<Introduction>

The dMEFs were infected with the retrovirus to thereby introduce the gene(s). The infection was performed in the following manner.

The dMEFs were seeded in a 12-well plate at $1 \times 10^5$ cells per well.

On the following day, an 8 mg/mL polybrene solution (available from Sigma, 107689) was added to the culture supernatant containing viral particles, which was collected as described under the section entitled "Production of retrovirus", at a final concentration of 8 μg/mL. The culture supernatant of the dMEFs was removed through aspiration, and then the below-described viral solutions were added to a 12-well plate (200 μL per well). Amounts of the viral solutions were adjusted so as to be uniform for each well with a DMEM (containing 10% FBS) solution containing 8 μg/mL polybrene. After the addition of the viral solutions, the resultant solutions were incubated within an incubator with 5% $CO_2$ at 37° C. During the incubation, the media were changed every 2 or 3 days.

[Viral Solution]

(1) pMX-GLIS1 vector-derived viral solution (hereinafter may be referred to as "G1 solution");

(2) pMX-Neurogenin3 vector-derived viral solution (hereinafter may be referred to as "N solution");

(3) pMX-Pdx1 vector-derived viral solution (hereinafter may be referred to as "P solution");

(4) pMX-Neurogenin3 vector-derived viral solution and pMX-Pdx1 vector-derived viral solution (hereinafter may be referred to as "NP solution");

(5) pMX-GLIS1 vector-derived viral solution and pMX-Neurogenin3 vector-derived viral solution (hereinafter may be referred to as "G1N solution");

(6) pMX-GLIS1 vector-derived viral solution and pMX-Pdx1 vector-derived viral solution (hereinafter may be referred to as "G1P solution");

(7) pMX-GLIS1 vector-derived viral solution, pMX-Neurogenin3 vector-derived viral solution, and pMX-Pdx1 vector-derived viral solution (hereinafter may be referred to as "G1NP solution"); and (8) pMX-GFP vector-derived viral solution (control; hereinafter may be referred to as "GFP CTL solution").

<Observation of dMEF-Derived Insulin Producing Cells and Counting of Number of Cells>

After the introduction and several days of culturing, DsRed2-positive insulin producing cells were observed and photographed by a fluorescence microscope (CARL ZEISS AXIOVERT 200M) unit.

A statistical analysis was performed in the following manner. HOECHST 33342 (available from Life Technologies Corporation, H1399) was added to wells of a cell culture multi-well plate at a final concentration of 0.1 μg/mL and incubated within an incubator with 5% $CO_2$ at 37° C. for 30 min or longer. Then, images were taken in 100 fields of view for each well using a high-end cell imaging apparatus (available from Thermo Fisher Scientific Inc., ARRAYSCAN XTI) with a 10× objective lens. The number of the DsRed2-positive insulin producing cells relative to the number of total cells was determined in the 100 fields of view.

<Result-1>

Two days after the introduction, observation was made by a fluorescence microscope (CARL ZEISS AXIOVERT 200M) unit. In the case where the G1N solution or the G1NP solution was used as the viral solution, fluorescence from DsRed2 was observed. Therefore, it was demonstrated that β cells, which are pancreatic endocrine cells, were capable of being produced from fibroblasts in a short period of time of 2 days when the G1N solution or the G1NP solution was used as the viral solution.

<Result-2>

The results of the statistical analysis performed 12 days after the introduction are presented in FIG. 1. In FIG. 1, the horizontal axis represents the viral solution used, that is, the results of the G1 solution, the N solution, the P solution, the NP solution, the G1N solution, and the G1NP solution were presented from left to right. Note that, the vertical axis represents the number of the DsRed2-positive insulin producing cells per well.

It can be seen from the results of FIG. 1 that the number of the β cells, which were pancreatic endocrine cells, was significantly increased in the case where (I) the GLIS1 gene and the Ngn3 gene or (II) the GLIS1 gene, the Ngn3 gene, and the Pdx1 gene were introduced into somatic cells. Therefore, it was demonstrated that pancreatic endocrine cells were capable of being produced from somatic cells in large quantities by introducing (I) the GLIS1 gene and the Ngn3 gene or (II) the GLIS1 gene, the Ngn3 gene, and the Pdx1 gene into the somatic cells.

<Result-3>

The results of the statistical analysis performed 17 days after the introduction are presented in Table 1.

TABLE 1

|   |   | Number of DsRed2-positive insulin producing cells/well | Rate of number of DsRed2-positive insulin producing cells relative to number of total cells |
|---|---|---|---|
| Viral solution | G1 solution | 169 | 0.12% |
|  | N solution | 802 | 1.2% |
|  | P solution | 89 | 0.09% |
|  | NP solution | 479 | 0.78% |

TABLE 1-continued

|  | Number of DsRed2-positive insulin producing cells/well | Rate of number of DsRed2-positive insulin producing cells relative to number of total cells |
|---|---|---|
| G1N solution | 11809 | 11.8% |
| G1P solution | 78 | 0.07% |
| G1NP solution-1 | 7055 | 8.5% |
| GFP CTL solution | 106 | 0.17% |
| G1NP solution-2 | 6554 | 7.81% |
| No viral infection | 5 | 0.01% |

It can be seen from the results of Table 1 that the rate of the number of the β cells, which were pancreatic endocrine cells, relative to the number of total cells was increased in the case where (I) the GLIS1 gene and the Ngn3 gene or (II) the GLIS1 gene, the Ngn3 gene, and the Pdx1 gene were introduced into somatic cells. Therefore, it was demonstrated that pancreatic endocrine cells were capable of being efficiently produced from somatic cells by introducing (I) the GLIS1 gene and the Ngn3 gene or (II) the GLIS1 gene, the Ngn3 gene, and the Pdx1 gene into the somatic cells.

Test Example 2: Production of Pancreatic Endocrine Cells from Mouse Fibroblasts-2

<Preparation of Cells>
The dMEFs were prepared in the same manner as in the Test Example 1.
<Production of Retrovirus>
The pMX-GLIS1 vector-derived viral solution, the pMX-Neurogenin3 vector-derived viral solution, and the pMX-Pdx1 vector-derived viral solution were produced in the same manner as in the Test Example 1.
<Introduction>
The genes were introduced into the dMEFs by infecting the cells with the retrovirus using the G1NP solution as the viral solution in the same manner as in the Test Example 1.
<Immunostaining Analysis>
An immunostaining analysis was performed using cells 21 days after the introduction to examine expression of insulin, glucagon, somatostatin, and Pdx1.
Specifically, the cells were fixed with a 4% paraformaldehyde solution at room temperature for 10 min, dipped into a 0.2% Triton-X/PBS solution at room temperature for 10 min, and then treated with 4-fold diluted BLOCKING ONE solution (available from NACALAI TESQUE, INC.) at room temperature for 1 hour. Then, a primary antibody reaction was performed with an anti-insulin antibody (400-fold diluted, guinea pig, available from DAKO), an anti-glucagon antibody (400-fold diluted, rabbit, available from DAKO), an anti-somatostatin antibody (500-fold diluted, rabbit, available from DAKO), or an anti-Pdx1 antibody (1,000-fold diluted, rabbit, obtained from Vanderbilt University, USA) at 4° C. overnight. Then, the resultant reaction products were washed with PBS 3 times at room temperature for 5 min, and subjected to a secondary antibody reaction with AlexaFluor-Cy3-labeled anti-rabbit antibody (400-fold diluted, available from Invitrogen) or AlexaFluor-488-labeled anti-guinea pig antibody (400-fold diluted, available from Invitrogen) at room temperature for 1 hour. The resultant reaction products were washed with PBS 3 times for 5 min, and then observed and photographed by an inverted fluorescence microscope (CARL ZEISS AXIOVERT 200M).

Figure 2A:
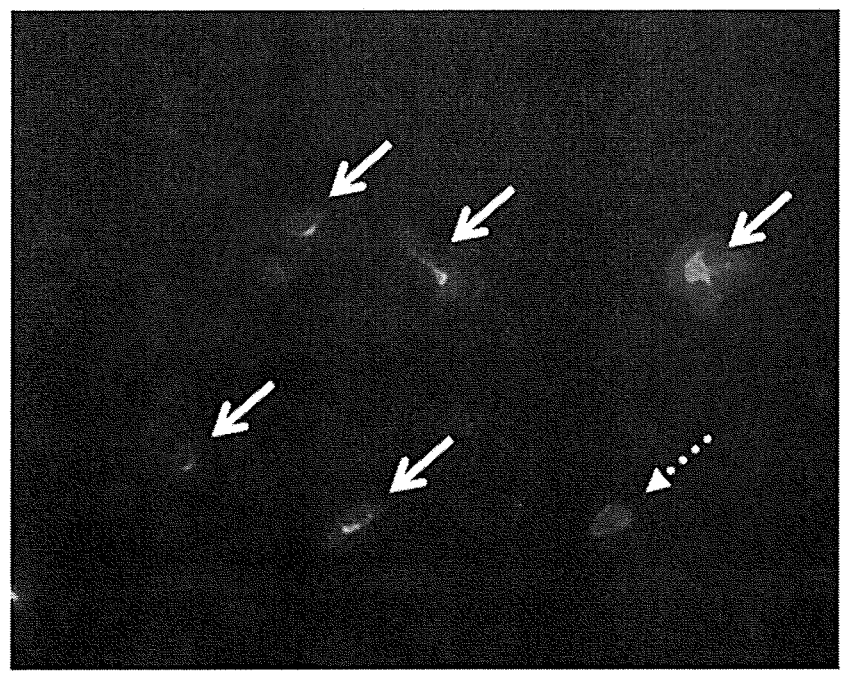
FIG. 2A is an image illustrating the analysis results of expression of insulin and somatostatin in Test Examples 2.
Figure 2B:
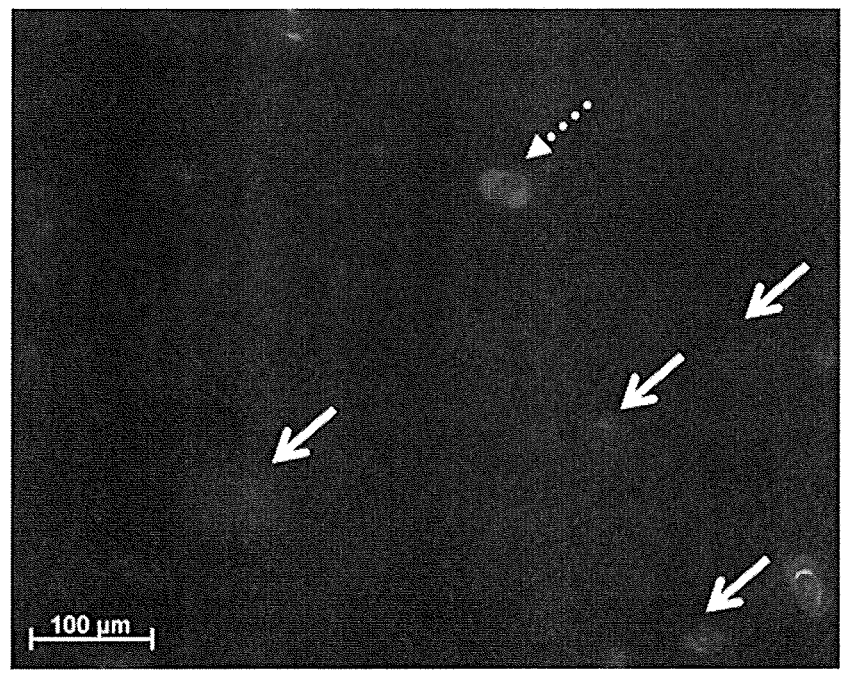
FIG. 2B is an image illustrating the analysis results of expression of insulin and glucagon in Test Examples 2.
Figure 2C:
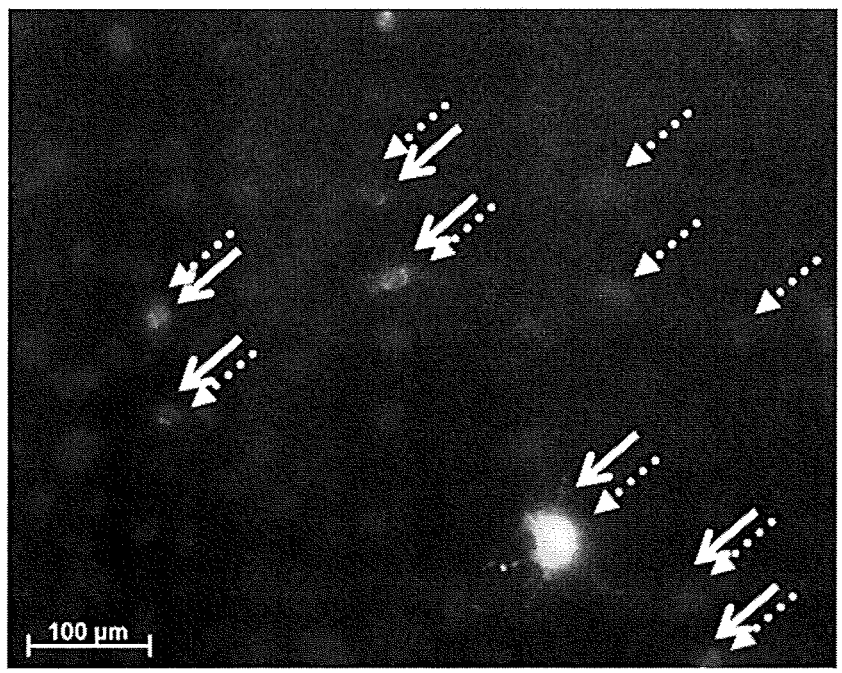
FIG. 2C is an image illustrating the analysis results of expression of insulin and Pdx1 in Test Examples 2.

The results of the immunostaining analysis are presented in FIGS. 2A to 2C. FIG. 2A illustrates the expression analysis results of insulin and somatostatin; FIG. 2B illustrates the expression analysis results of insulin and glucagon; and FIG. 2C illustrates the expression analysis results of insulin and Pdx1. In FIGS. 2A to 2C, the arrows with a solid line represent cells in which insulin expression is confirmed. In FIGS. 2A to 2C, the arrows with a dashed line represent cells in which somatostatin expression in FIG. 2A, glucagon expression in FIG. 2B, or Pdx1 expression in FIG. 2C is confirmed.

It was confirmed from the results of FIGS. 2A to 2C that glucagon to be expressed in α cells, insulin to be expressed in β cells, and somatostatin to be expressed in δ cells were expressed at the protein level. Additionally, Pdx1, which is necessary for pancreatic development, was also confirmed to be expressed at the protein level.

Therefore, it was demonstrated that not only β cells, which are insulin producing cells, but also α cells and δ cells are capable of being produced by the method of the present invention.

Test Example 3: Production of Pancreatic Endocrine Cells from Various Somatic Cells-1

<Preparation of Cells>
The following cells were prepared.
(1) dMEF
Prepared in the same manner as in Test Example 1.
(2) Human iPS (253G13-6)-Derived Fibroblasts
Obtained from Riken BioResource Center.
(3) Human HepG2 (Human Hepatoma-Derived Cell Line)
Obtained from Riken BioResource Center.
(4) Mouse NIH-3T3 (Cultured Cells Isolated from Mouse Embryonic Skin)
Obtained from Riken BioResource Center.
(5) Human Embryonic Fibroblasts (FHDF)
Obtained from TOYOBO CO., LTD.
(6) Human Neonatal Fibroblasts (NHDF)
Obtained from TAIKARA SHUZO CO., LTD.
(7) Human HEK293 (Cell Line Established by Transforming Human Embryonic Renal Cells with Adenovirus E1 Gene)
Obtained from Riken BioResource Center.
<Production of Retrovirus>
—Production of Retrovirus for Mouse Cells—
The pMX-GLIS1 vector-derived viral solution, the pMX-Neurogenin3 vector-derived viral solution, and the pMX-GFP vector-derived viral solution were produced for mouse cells in the same manner as in the Test Example 1.
—Production of Retrovirus for Human Cells—
Plat-GP cells in which viral structural proteins gag-pol and env, which were capable of producing high titer viruses for a long period of time, were expressed under the control of MoMuLV LTR and a plasmid DNA (pMX vector or pMX-puro vector, VSVG vector) were used to produce a retrovirus in the following manner (Onishi, M., et. al., Exp. Hematol. 24, 324-329, 1996).
——Preparation of Plasmid DNA——
[pMX-GFP Vector]
The pMX-GFP vector was prepared in the same manner as in the Test Example 1.
[pMX-GLIS1 Vector]
The pMX-GLIS1 vector was prepared in the same manner as in the Test Example 1, except that the sequence of the gene coding for a full-length GLIS1 protein deposited under Accession number NM_147221 was changed to the sequence of the gene coding for a full-length GLIS1 protein deposited under Accession number NM_147193.

[pMX-Neurogenin3 Vector]

The pMX-Neurogenin3 vector was prepared in the same manner as in the Test Example 1, except that the sequence of the gene coding for a full-length Neurogenin3 protein deposited under Accession number NM_009719 was changed to the sequence of the gene coding for a full-length Neurogenin3 protein deposited under Accession number NM 020999.

[pMX-Pdx1 Vector]

The pMX-Pdx1 vector was prepared in the same manner as in the Test Example 1, except that the sequence of the gene coding for a full-length Pdx1 protein deposited under Accession number NM_008814 was changed to the sequence of the gene coding for a full-length Pdx1 protein deposited under Accession number NM_000209.

——Production of Retrovirus——

The Plat-GP cells were seeded in a 6-well plate (available from TPP, 92406), which had been coated (for 1 hour at 37° C. and 5% $CO_2$) with Poly-L-Lysine (available from Sigma, P8920) diluted 10 fold with PBS, at $8 \times 10^5$ cells per well, and cultured overnight.

On the following day, 4 μg of the plasmid DNA (2 μg of the pMX vector and 2 μg of the VSVG vector) was placed into a 1.5 mL tube containing 250 μL of OPTI-MEM (registered trademark) (available from Life Technologies Corporation, 11058021), mixed by tapping, and left to stand at room temperature for 5 min (hereinafter may be referred to as "plasmid/OPTI-MEM solution"). Meanwhile, 10 μL of LIPOFECTAMINE (registered trademark) 2000 (LP2000) (available from Life Technologies Corporation, 11668500) was placed into another 1.5 mL tube containing 250 μL of OPTI-MEM, mixed together, and left to stand at room temperature for 5 min (hereinafter may be referred to as "LP2000/OPTI-MEM solution"). The plasmid/OPTI-MEM solution and the LP2000/OPTI-MEM solution were well-mixed together and left to stand at room temperature for 20 min (hereinafter may be referred to as "plasmid/LP2000/OPTI-MEM mixed solution").

The plasmid/LP2000/OPTI-MEM mixed solution in which liposome-DNA complexes had been formed was added to one well in the 6-well plate, in which the Plat-GP cells seeded the previous day had been cultured, to thereby transfect the cells. After mixing, the cells were cultured within an incubator with 5% $CO_2$ at 37° C. overnight. Twenty-four hours after, the medium was replaced, 1.5 mL of fresh DMEM (containing 10% FBS) was added thereto, and further cultured for 24 hours.

Forty-eight hours after the transfection, the culture supernatant containing viral particles was collected in a 2.5 mL syringe (available from Terumo Corporation, SS-02SZ) and filtered through a 0.45 filter (available from Whatman, PURADISC FP30 (CA-S 0.45 μm), 10462100) to thereby remove the Plat-GP cells. The culture supernatant containing viral particles were transferred into a 2.0 mL tube.

Thus, a pMX-GLIS1 vector-derived viral solution, a pMX-Neurogenin3 vector-derived viral solution, a pMX-Pdx1 vector-derived viral solution, and a pMX-GFP vector-derived viral solution for human cells were obtained.

<Introduction>

The genes were introduced into the cells by infecting the cells with the retrovirus using the G1N solution or the GFP CTL solution as the viral solution in the same manner as in the Test Example 1.

<Quantitative PCR Analysis>

A quantitative PCR analysis was performed as described below using the cells 20 days after the introduction to thereby determine a relative expression level of an insulin gene relative to a GAPDH gene.

The cells were suspended in α cell lysis solution, and subjected to RNA preparation and cDNA synthesis using SuperPrep™ Cell Lysis & RT Kit for qPCR (available from TOYOBO CO., LTD., # SCQ-101) or SV 96 Total RNA Isolation System (available from Promega, # Z3505), Rever-TraAce qPCR RT Master Mix with gDNA Remover (available from TOYOBO CO., LTD., # FSQ-301) and then the quantitative PCR analysis using GeneAce SYBR qPCR Mixa (available from NIPPON GENE CO., LTD.).

Note that, the following primers were used for the quantitative PCR analysis.

```
Mouse GAPDH gene-
Forward:
                                    (SEQ ID NO: 1)
5'-tggagaaacctgcaagtatg-3'

Reverse:
                                    (SEQ ID NO: 2)
5'-ggagacaacctggtcctcag-3'

Mouse insulin2 gene-
Forward:
                                    (SEQ ID NO: 3)
5'-tttgtcaagcagcacctttg-3'

Reverse:
                                    (SEQ ID NO: 4)
5'-ggtctgaaggtcacctgctc-3'

Human GAPDH gene-
Forward:
                                    (SEQ ID NO: 5)
5'-atgttcgtcatgggtgtgaa-3'

Reverse:
                                    (SEQ ID NO: 6)
5'-tgtggtcatgagtccttcca-3'

Human insulin gene-
Forward:
                                    (SEQ ID NO: 7)
5'-gccatcaagcagatcactgt-3'

Reverse:
                                    (SEQ ID NO: 8)
5'-caggtgttggttcacaaagg-3'
```

Figure 3A:
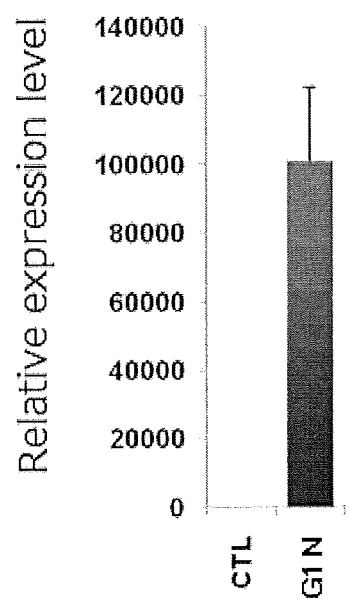
FIG. 3A is a graph illustrating the results in dMEFs in Test Example 3.
Figure 3B:
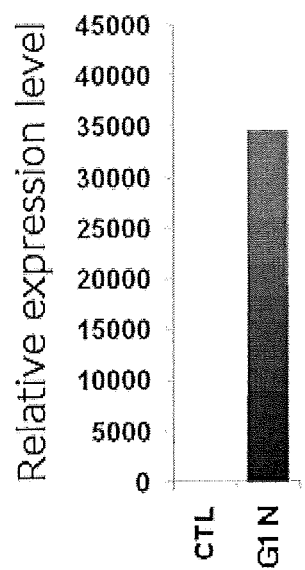
FIG. 3B is a graph illustrating the results in human iPS (253G13-6)-derived fibroblasts in Test Example 3.
Figure 3C:
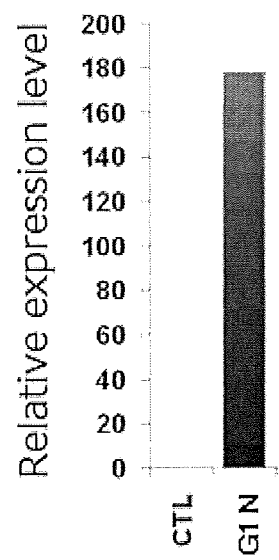
FIG. 3C is a graph illustrating the results in human HepG2 in Test Example 3.
Figure 3D:
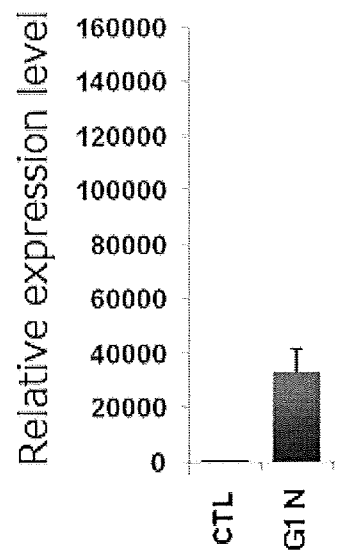
FIG. 3D is a graph illustrating the results in mouse NIH-3T3 in Test Example 3.
Figure 3E:
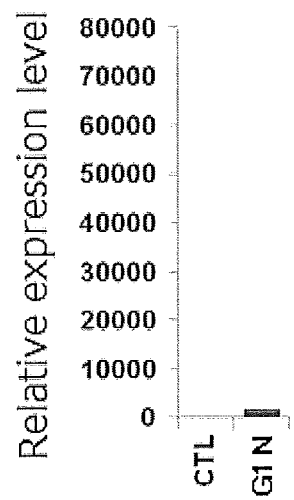
FIG. 3E is a graph illustrating the results in human embryonic fibroblasts in Test Example 3.
Figure 3F:
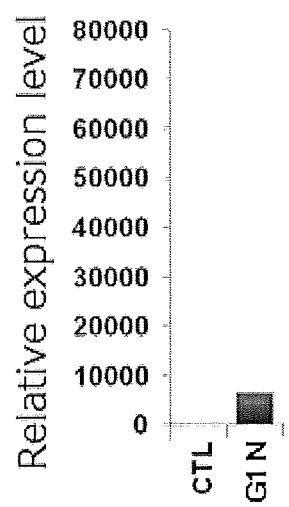
FIG. 3F is a graph illustrating the results in human neonatal fibroblasts in Test Example 3.
Figure 3G:
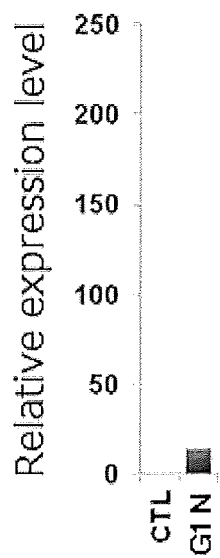
FIG. 3G is a graph illustrating the results in human HEK293 in Test Example 3.

The results of the quantitative PCR analysis are presented in FIGS. 3A to 3G. FIG. 3A illustrates the results of the dMEFs; FIG. 3B illustrates the results of the human iPS (253G13-6)-derived fibroblasts; FIG. 3C illustrates the results of the human HepG2; FIG. 3D illustrates the results of the mouse NIH-3T3; FIG. 3E illustrates the results of the human embryonic fibroblasts; FIG. 3F illustrates the results of the human neonatal fibroblasts; and FIG. 3G illustrates the results of the human HEK293. In FIGS. 3A to 3G, CTL represents the results in the case of using the GFP CTL solution and G1N represents the results in the case of using the G1N solution. Note that, the vertical axis represents the relative expression level of an insulin gene relative to a GAPDH gene.

It was confirmed from the results of FIGS. 3A to 3G that other cells than mouse fibroblasts also expressed the insulin gene by using the G1N solution.

Therefore, it was demonstrated that pancreatic endocrine cells were capable of being produced from various somatic cells by the method of the present invention.

Test Example 4: Transdifferentiation Potency of GLIS Family

<Preparation of Cells>

The dMEFs were prepared in the same manner as in the Test Example 1.

<Production of Retrovirus>

—Preparation of Plasmid DNA—

[pMX-GFP Vector]

The pMX-GFP vector was prepared in the same manner as in the Test Example 1.

[pMX-GLIS1 Vector]

The pMX-GLIS1 vector was prepared in the same manner as in the Test Example 1.

[pMX-GLIS3 Vector]

A pMX-GLIS3 vector is a vector in which a gene coding for a full-length GLIS3 protein is inserted into a multi-cloning site of a pMX vector (obtained from The Institute of Medical Science, The University of Tokyo). Note that, the sequence of the gene coding for a full-length GLIS3 protein is deposited in NCBI under Accession number NM 175459.

[pMX-Neurogenin3 Vector]

The pMX-Neurogenin3 vector was prepared in the same manner as in the Test Example 1.

[pMX-Pdx1 Vector]

The pMX-Pdx1 vector was prepared in the same manner as in the Test Example 1.

—Production of Retrovirus—

A culture supernatant containing viral particles was prepared in the same manner as in the Test Example 1, except that the plasmid DNA was used. The resultant culture supernatant was used as a viral solution.

<Introduction>

The genes were introduced into the dMEFs by infecting the cells with the retrovirus in the same manner as in the Test Example 1, except that the following viral solutions were used.

[Viral Solution]

(1) pMX-GFP vector-derived viral solution (control, hereinafter may be referred to as "GFP CTL solution");
(2) pMX-GLIS1 vector-derived viral solution (hereinafter may be referred to as "G1 solution");
(3) pMX-GLIS3 vector-derived viral solution (hereinafter may be referred to as "G3 solution");
(4) pMX-GLIS1 vector-derived viral solution and pMX-Neurogenin3 vector-derived viral solution (hereinafter may be referred to as "G1N solution");
(5) pMX-GLIS3 vector-derived viral solution and pMX-Neurogenin3 vector-derived viral solution (hereinafter may be referred to as "G3N solution");
(6) pMX-GLIS1 vector-derived viral solution, pMX-Neurogenin3 vector-derived viral solution, and pMX-Pdx1 vector-derived viral solution (hereinafter may be referred to as "G1NP solution"); and
(7) pMX-GLIS3 vector-derived viral solution, pMX-Neurogenin3 vector-derived viral solution, and pMX-Pdx1 vector-derived viral solution (hereinafter may be referred to as "G3NP solution").

<Counting of Number of dMEF-Derived Insulin Producing Cells>

The number of the DsRed2-positive insulin producing cells was counted in the same manner as in the Test Example 1, except that cells 11 days after the introduction were used.

Figure 4A:
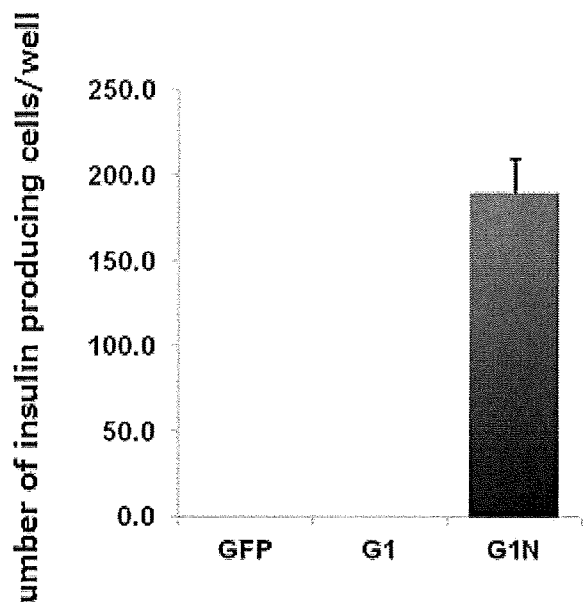
FIG. 4A is a graph-1 illustrating the results in Test Example 4.
Figure 4B:
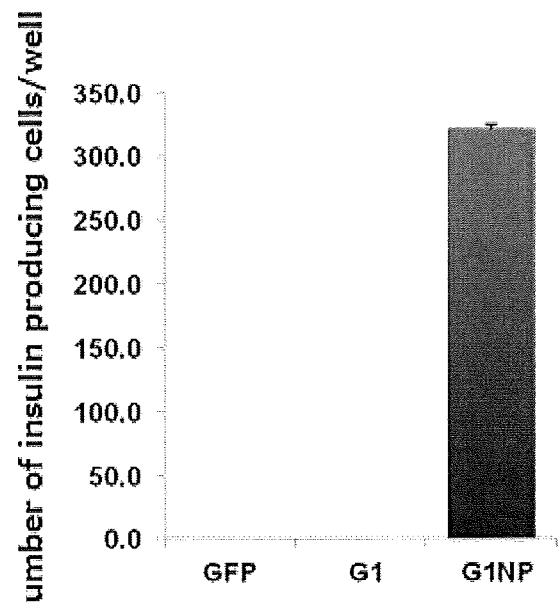
FIG. 4B is a graph-2 illustrating the results in Test Example 4.
Figure 4C:
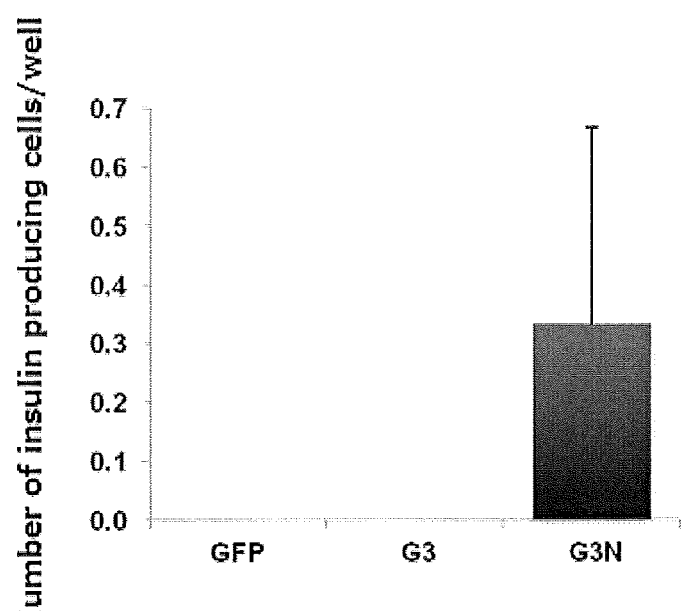
FIG. 4C is a graph-3 illustrating the results in Test Example 4.
Figure 4D:
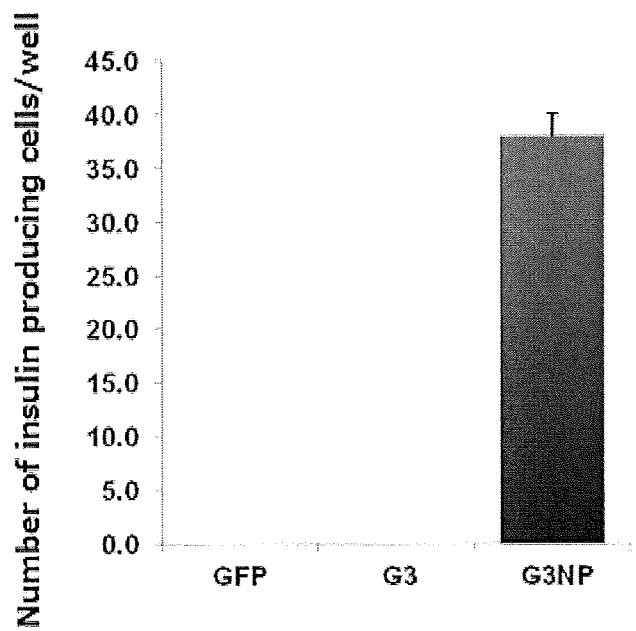
FIG. 4D is a graph-4 illustrating the results in Test Example 4.

The counting results of the DsRed2-positive insulin producing cells are presented in FIGS. 4A to 4D. FIG. 4A illustrates the results in the case of using the GFP CTL solution (GFP), the G1 solution (G1), and the G1N solution (G1N) as the viral solution from left to right; FIG. 4B illustrates the results in the case of using the GFP CTL solution (GFP), the G1 solution (G1), and the G1NP solution (G1NP) as the viral solution from left to right; FIG. 4C illustrates the results in the case of using the GFP CTL solution (GFP), the G3 solution (G3), and the G3N solution (G3N) as the viral solution from left to right; and FIG. 4D illustrates the results in the case of using the GFP CTL solution (GFP), the G3 solution (G3), and the G3NP solution (G3NP) as the viral solution from left to right. Note that, the vertical axis represents the number of the DsRed2-positive insulin producing cells per well.

It can be seen from the results of FIGS. 4A to 4D that, even when GLIS3, which was a member of a GLIS family, was used, pancreatic endocrine cells were capable of being produced by introducing along with Neurogenin3, or Neurogenin3 and Pdx1 into somatic cells. Therefore, it was suggested that pancreatic endocrine cells were capable of being produced by introducing the GLIS family along with Neurogenin3, or Neurogenin3 and Pdx1 into somatic cells. It was also demonstrated from comparison of GLIS1 with the GLIS3 that the GLIS1 yields about 10 times higher transdifferentiation efficiency than the GLIS3.

Test Example 5: Production of Pancreatic Endocrine Cells from Various Somatic Cells-2

<Preparation of Cells>

The following cells were prepared.

(1) Human T98G Glioblastoma
   Obtained from Riken BioResource Center.
(2) Human Mesenchymal Stem Cells
   Obtained from Lonza.

<Production of Retrovirus>

The pMX-GLIS1 vector-derived viral solution, the pMX-Neurogenin3 vector-derived viral solution, and the pMX-Pdx1 vector- and pMX-GFP vector-derived viral solution were produced in the same manner as Production of retrovirus for human cells in the Test Example 3.

<Introduction>

The genes were introduced into the cells by infecting the cells with the retrovirus using the GFP CTL solution, the G1N solution, or the G1NP solution as the viral solution in the same manner as in the Test Example 1.

<Quantitative PCR Analysis>

The quantitative PCR analysis was performed in the same manner as in the Test Example 3 to thereby determine a relative expression level of an insulin gene relative to a GAPDH gene.

Figure 5A:
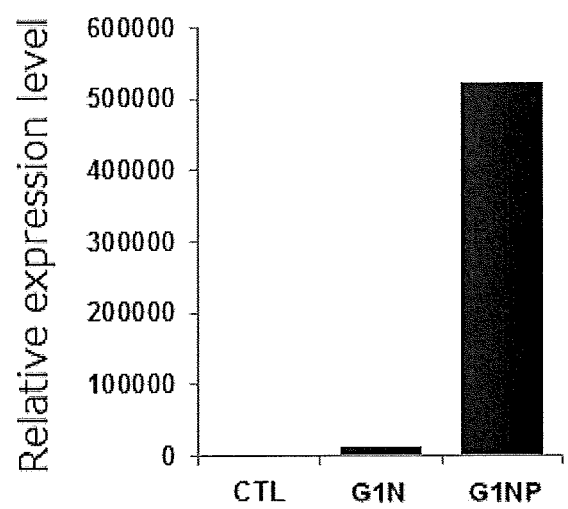
FIG. 5A is a graph illustrating the results in human T98G glioblastoma in Test Example 5.
Figure 5B:
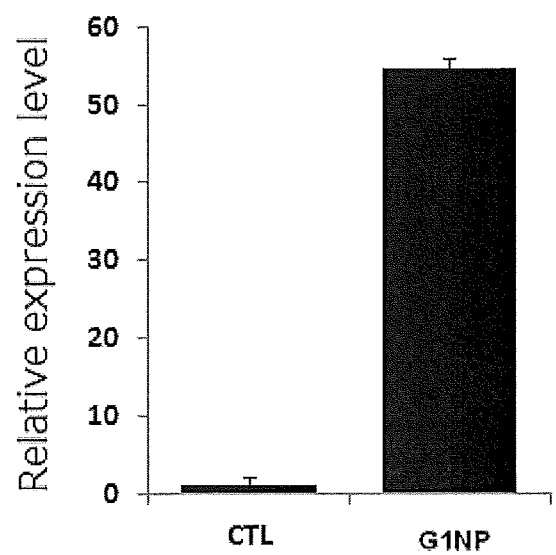
FIG. 5B is a graph illustrating the results in human mesenchymal stem cells in Test Example 5.

The results of the quantitative PCR analysis are presented in FIGS. 5A and 5B. FIG. 5A illustrates the results of the human T98G glioblastoma; and FIG. 5B illustrates the results of the human mesenchymal stem cells. In FIGS. 5A and 5B, CTL represents the results in the case of using the GFP CTL solution, G1N represents the results in the case of using the G1N solution, and G1NP represents the results in the case of using the G1NP solution. Note that, the vertical axis represents the relative expression level of an insulin gene relative to a GAPDH gene.

It was confirmed from the results of FIGS. 5A and 5B that the insulin gene was expressed also in the human T98G glioblastoma and the human mesenchymal stem cells by using the G1N solution or the G1NP solution.

Therefore, it was demonstrated that pancreatic endocrine cells were capable of being produced from various somatic cells by the method of the present invention.

Test Example 6: Comparison with Mouse Pancreatic Islets

<Preparation of Cells>

The dMEFs were prepared in the same manner as in the Test Example 1.

<Production of Retrovirus>

The pMX-GLIS1 vector-derived viral solution, the pMX-Neurogenin3 vector-derived viral solution, and the pMX-Pdx1 vector-derived viral solution were produced in the same manner as in the Test Example 1.

<Introduction>

The genes were introduced into the dMEFs by infecting the cells with the retrovirus using the G1NP solution as the viral solution in the same manner as in the Test Example 1.

<Microscopic Observation>

Cells 16 days after the introduction were observed by a microscopy (FLUO™, available from Leica, AXIOCAM HRC, available from CARL ZEISS, magnification of ×4). Pancreatic islets isolated from mouse pancreas were also observed by the microscopy.

Figure 6A:
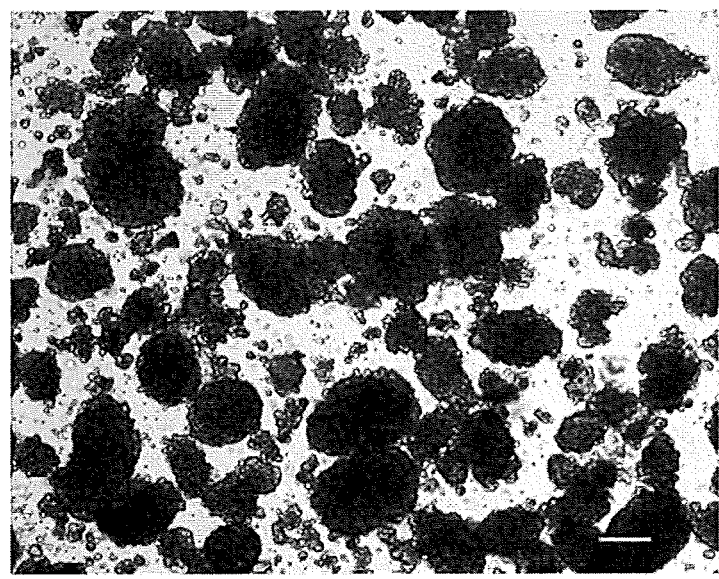
FIG. 6A is an image illustrating a pancreatic islet isolated from a mouse pancreas in Test Example 6.
Figure 6B:
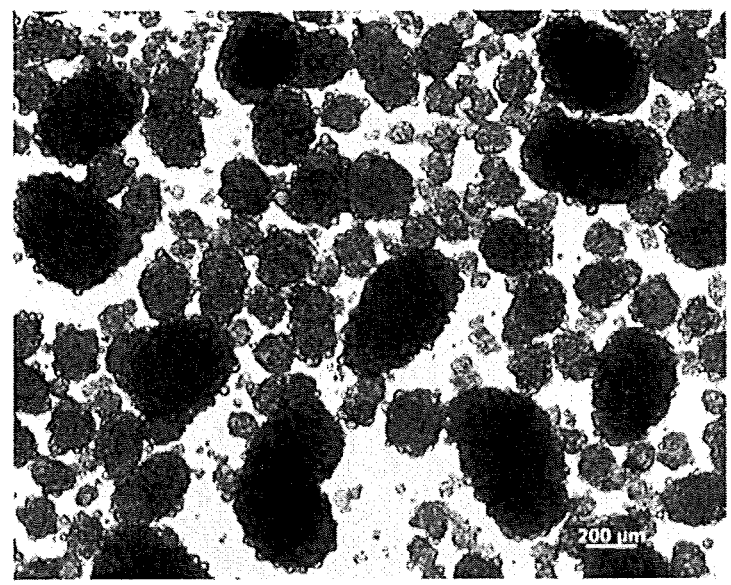
FIG. 6B is an image illustrating dMEFs infected with a retrovirus using a G1NP solution as a viral solution in Test Example 6.

The results of the microscopic observation are presented in FIGS. 6A and 6B. FIG. 6A illustrates a pancreatic islet isolated from a mouse pancreas and FIG. 6B illustrates the result in the case of using the G1NP solution as the viral solution.

It was confirmed from the results of FIGS. 6A and 6B that pancreatic endocrine cell masses obtained by the method of the present invention resemble pancreatic islets isolated from mouse pancreas.

Test Example 7: Glucose-Responsive Insulin Secretion Test-1

<Preparation of Cells>

The dMEFs were prepared in the same manner as in the Test Example 1.

<Production of Retrovirus>

The pMX-GLIS1 vector-derived viral solution, the pMX-Neurogenin3 vector-derived viral solution, and the pMX-Pdx1 vector-derived viral solution were produced in the same manner as in the Test Example 1.

<Introduction>

The genes were introduced into the dMEFs by infecting the cells with the retrovirus using the G1NP solution as the viral solution in the same manner as in the Test Example 1.

<Glucose-Responsive Insulin Secretion Test>

Twenty-seven days after the introduction, 30 uniform pancreatic islet-like masses having a diameter of 100 μm to 300 μm were picked up by a pipette under a stereoscopic microscope and transferred into a 24-well plate. Then, a glucose-responsive insulin secretion test was performed in the same manner.

The pancreatic islet-like masses were cultured in a 2.8 mM glucose-containing Ringer's solution for 3 hours. Then, the medium was replaced and the masses were cultured for another 1 hour, of which culture supernatants were used as a reference (hereinafter may be referred to as "reference culture supernatant").

Then, the pancreatic islet-like masses were cultured in a 16.8 mM glucose-containing Ringer's solution for 1 hour. A culture supernatants thereof were transferred into a 1.5 mL tube (hereinafter may be referred to as "high-glucose culture supernatant").

Then, a 2.8 mM glucose-containing Ringer's solution was added to wells, where the pancreatic islet-like masses were cultured for 1 hour. A culture supernatants thereof were transferred into a 1.5 mL tube (hereinafter may be referred to as "low-glucose culture supernatant").

An insulin concentration in each of the culture supernatants was measured by ELISA assay (available from Shibayagi Co., Ltd., TYPE T). The results are presented in FIG. 7.

Figure 7:
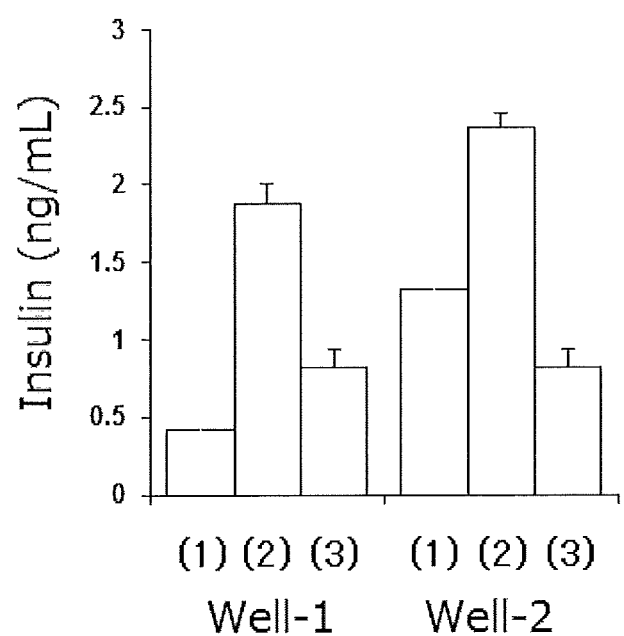
FIG. 7 is a graph illustrating the results of a glucose-responsive insulin secretion test in Test Example 7.

FIG. 7 illustrates the results for each of two wells. In FIG. 7, (1) illustrates the result of the reference culture supernatant, (2) illustrates the result of the high-glucose culture supernatant, and (3) illustrates the result of the low-glucose culture supernatant.

It was confirmed from the results of FIG. 7 that an amount of insulin was increased at a higher glucose concentration and a concentration of insulin was decreased at a lower glucose concentration. Therefore, the pancreatic endocrine cells obtained by the method of the present invention were confirmed to have functions required for pancreatic endocrine cells.

Test Example 8: Glucose-Responsive Insulin Secretion Test-2

<Preparation of Cells>

Human neonatal fibroblasts (NHDF) (available from TAKARA SHUZO CO., LTD.) were prepared.

<Production of Retrovirus>

The pMX-GLIS1 vector-derived viral solution, the pMX-Neurogenin3 vector-derived viral solution, and the pMX-Pdx1 vector-derived viral solution were produced in the same manner as in Production of retrovirus for human cells in the Test Example 3.

<Introduction>

The genes were introduced into the human neonatal fibroblasts (NHDF) by infecting the cells with the retrovirus in the same manner as in the Test Example 1, except that the G1NP solution was used as the viral solution and a 24-well plate was used.

<Glucose-Responsive Insulin Secretion Test>

Thirty-four days after the introduction, the entire pancreatic islet-like mass was picked up by a pipette and transferred into a 24-well plate (low attachment plate (EZ-BINDSHUT II, available from IWAKI)). Then, a glucose-responsive insulin secretion test was performed in the following manner.

The pancreatic islet-like mass was cultured in a 2.8 mM glucose-containing Ringer's solution for 3 hours. Then, the medium was replaced and the mass was cultured for another 1 hour, of which culture supernatant was used as a reference (hereinafter may be referred to as "reference culture supernatant").

Then, the pancreatic islet-like mass was cultured in a 25.0 mM glucose-containing Ringer's solution for 1 hour. A culture supernatant thereof was transferred into a 1.5 mL tube (hereinafter may be referred to as "high-glucose culture supernatant").

An insulin concentration in each of the culture supernatants was measured by ELISA assay (human insulin ELISA kit, available from Mercodia). The results are presented in FIG. 8.

Figure 8:
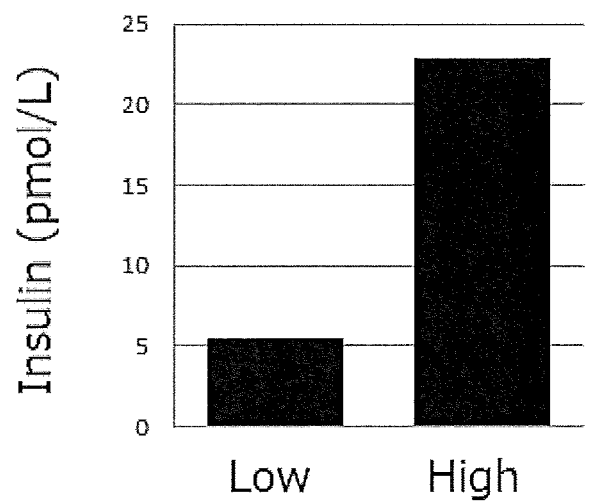
FIG. 8 is a graph illustrating the results of a glucose-responsive insulin secretion test in Test Example 8.

In FIG. 8, "Low" represents the result of the reference culture supernatant and "High" represents the result of the high-glucose culture supernatant.

It was confirmed from the results of FIG. 8 that, also in the case of using human-derived cells, an amount of insulin was increased at a higher glucose concentration and a concentration of insulin was decreased at a lower glucose concentration and that the resultant pancreatic endocrine cells had functions required for pancreatic endocrine cells.

Test Example 9: Production of Pancreatic Endocrine Cells Using Episomal Vector

<Preparation of Cells>

The dMEFs were prepared in the same manner as in the Test Example 1.

<Preparation of Episomal Vector>

[pCI-GFP Vector]

A pCI-GFP vector is a vector in which a gene coding for a full-length GFP protein is inserted into a multi-cloning site of a pCI vector (available from Promega) which is an episomal vector. Note that, the sequence of the gene coding for a full-length GFP protein is deposited in NCBI under Accession number L29345.

[pCI-GLIS1 Vector]

A pCI-GLIS1 vector is a vector in which a gene coding for a full-length GLIS1 protein is inserted into a multi-cloning site of a pCI vector (available from Promega) which is an episomal vector. Note that, the sequence of the gene coding for a full-length GLIS1 protein is deposited in NCBI under Accession number NM_147221.

[pCI-Neurogenin3 Vector]

A pCI-Neurogenin3 vector is a vector in which a gene coding for a full-length Neurogenin3 protein is inserted into a multi-cloning site of a pCI vector (available from Promega) which is an episomal vector. Note that, the sequence of the gene coding for a full-length Neurogenin3 protein is deposited in NCBI under Accession number NM 009719.

[pCI-Pdx1 Vector]

A pCI-Pdx1 vector is a vector in which a gene coding for a full-length Pdx1 protein is inserted into a multi-cloning site of a pCI vector (available from Promega) which is an episomal vector. Note that, the sequence of the gene coding for a full-length Pdx1 protein is deposited in NCBI under Accession number NM_008814.

<Introduction>

The following vectors were introduced into the dMEFs by electroporation using NEON (registered trademark) transfection system (available from Life Technologies Corporation). After the vectors were introduced, the cells were incubated within an incubator with 5% $CO_2$ at 37° C. During the incubation, the media (DMEM (containing 10% FBS)) were changed every 2 or 3 days.

[Vector]

(1) pCI-GFP vector (control, hereinafter may be referred to as "GFP");

(2) pCI-GLIS1 vector and pCI-Neurogenin3 vector (hereinafter may be referred to as "G1N"); and (3) pCI-GLIS1 vector, pCI-Neurogenin3 vector, and pCI-Pdx1 vector (hereinafter may be referred to as "G1NP").

<Counting of Number of dMEF-Derived Insulin Producing Cells>

The number of the DsRed2-positive insulin producing cells was counted in the same manner as in the Test Example 1, except that cells 8 days after the introduction were used.

Figure 9:
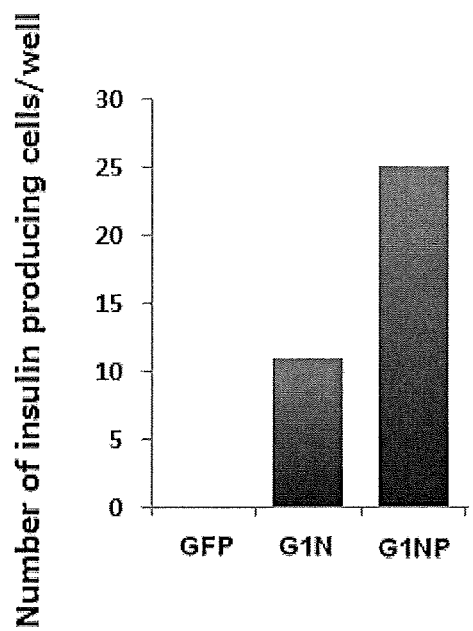
FIG. 9 is a graph illustrating the results in Test Example 9.

The counting results of the DsRed2-positive insulin producing cells are presented in FIG. 9. In FIG. 9, the horizontal axis represents the episomal vectors introduced, that is, the results of the GFP, the G1N, and the G1NP were presented from left to right. Note that, the vertical axis represents the number of DsRed2-positive insulin producing cells per well.

It was demonstrated from the results of FIG. 9 that, even when the episomal vectors were used, pancreatic endocrine cells were capable of being produced from somatic cells by introducing (I) the GLIS1 gene and the Ngn3 gene or (II) the GLIS1 gene, the Ngn3 gene, and the Pdx1 gene.

A method for producing pancreatic endocrine cells including introducing a gene or one or more gene products thereof into somatic cells according to the present invention is simple, is easily reproduced, and has a remarkably shortened production time compared to previous methods in which pancreatic endocrine cells are produced using ES cells or iPS cells under a culturing environment properly adjusted by, for example, adding a development inhibitor to a medium. According to the method of the present invention, the pancreatic endocrine cells are capable of efficiently produced.

The method of the present invention is also advantageous in that the pancreatic endocrine cells are capable of being produced without undergoing the iPS cell stage that have a risk of forming tumors.

Therefore, the method for producing pancreatic endocrine cells according to the present invention is suitably available for, for example, producing pancreatic endocrine cells to be used in regenerative therapies for diabetes.

Aspects of the present invention are, for example, as follows.

<1> A method for producing pancreatic endocrine cells, the method including
  introducing one or more genes of a GLIS family or one or more gene products thereof and a Neurogenin3 gene or one or more gene products thereof into somatic cells.

<2> The method for producing pancreatic endocrine cells according to <1>, wherein the introducing includes further introducing a Pdx1 gene or one or more gene products thereof into the somatic cells.

<3> The method for producing pancreatic endocrine cells according to <1> or <2>, wherein the one or more genes of the GLIS family or one or more gene products thereof are a GLIS1 gene or one or more gene products thereof.

<4> The method for producing pancreatic endocrine cells according to any one of <1> to <3>, wherein the somatic cells are fibroblasts or mesenchymal stem cells.

<5> The method for producing pancreatic endocrine cells according to any one of <1> to <4>, wherein the pancreatic endocrine cells are β cells.

<6> Pancreatic endocrine cells produced by the method for producing pancreatic endocrine cells according to any one of <1> to <5>.

<7> The pancreatic endocrine cells according to <6>, wherein the pancreatic endocrine cells include β cells.

<8> A transdifferentiation agent including:
  one or more genes of a GLIS family or one or more gene products thereof; and
  a Neurogenin3 gene or one or more gene products thereof,
  wherein the transdifferentiation agent is configured to transdifferentiate somatic cells into pancreatic endocrine cells.

<9> The transdifferentiation agent according to <8>, further including a Pdx1 gene or one or more gene products thereof.

<10> The transdifferentiation agent according to <8> or <9>, wherein the one or more genes of the GLIS family or one or more gene products thereof is a GLIS1 gene or one or more gene products thereof.

<11> The transdifferentiation agent according to any one of <8> to <10>, wherein the somatic cells are fibroblasts or mesenchymal stem cells.

<12> The transdifferentiation agent according to any one of <8> to <11>, wherein the pancreatic endocrine cells are β cells.

The invention claimed is:

1. A method for transdifferentiating somatic cells into pancreatic endocrine cells, the method comprising
introducing one or more genes of a GLIS family or one or more gene products thereof and a Neurogenin3 gene or one or more gene products thereof into the somatic cells,
wherein the one or more genes of a GLIS family or one or more gene products thereof is selected from the group consisting of GLIS1 and GLIS3 and wherein the somatic cells transdifferentiate into the pancreatic endocrine cells without undergoing an iPS cell stage.

2. The method for transdifferentiating somatic cells into pancreatic endocrine cells according to claim 1, wherein the introducing includes further introducing a Pdx1 gene or one or more gene products thereof into the somatic cells.

3. The method for transdifferentiating somatic cells into pancreatic endocrine cells according to claim 2, which introduces a GLIS1 gene or one or more gene products thereof, a Neurogenin3 gene or one or more gene products thereof, and a Pdx1 gene or one or more gene products thereof into the somatic cells.

4. The method for transdifferentiating somatic cells into pancreatic endocrine cells according to claim 2, which introduces a GLIS3 gene or one or more gene products thereof, a Neurogenin3 gene or one or more gene products thereof, and a Pdx1 gene or one or more gene products thereof into the somatic cells.

5. The method for transdifferentiating somatic cells into pancreatic endocrine cells according to claim 1, wherein the one or more genes of the GLIS family or one or more gene products thereof are a GLIS1 gene or one or more gene products thereof.

6. The method for transdifferentiating somatic cells into pancreatic endocrine cells according to claim 1, wherein the somatic cells are fibroblasts or mesenchymal stem cells.

7. The method for transdifferentiating somatic cells into pancreatic endocrine cells according to claim 1, wherein the pancreatic endocrine cells are cells.

8. The method for transdifferentiating somatic cells into pancreatic endocrine cells according to claim 1, which introduces a GLIS1 gene or one or more gene products thereof and a Neurogenin3 gene or one or more gene products thereof into the somatic cells.

* * * * *

UNITED STATES PATENT AND TRADEMARK OFFICE
CERTIFICATE OF CORRECTION

PATENT NO. : 10,793,832 B2
APPLICATION NO. : 16/243865
DATED : October 6, 2020
INVENTOR(S) : Matsumoto et al.

It is certified that error appears in the above-identified patent and that said Letters Patent is hereby corrected as shown below:

In the Claims

Claim 7, Column 28, Line 34: Delete: "wherein the pancreatic endocrine cells are cells" and insert -- wherein the pancreatic endocrine cells are β cells --.

Signed and Sealed this
Nineteenth Day of October, 2021

Drew Hirshfeld
*Performing the Functions and Duties of the
Under Secretary of Commerce for Intellectual Property and
Director of the United States Patent and Trademark Office*